United States Patent [19]

Del Rossi et al.

[11] Patent Number: 5,107,054
[45] Date of Patent: Apr. 21, 1992

[54] ZEOLITE MCM-22 BASED CATALYST FOR PARAFFIN ISOMERIZATION

[75] Inventors: Kenneth J. Del Rossi, Mantua, N.J.; Albin Huss, Jr., Chadds Ford, Pa.; Garry W. Kirker, Washington Township, Burlington County, N.J.

[73] Assignee: Mobil Oil Corporation, Fairfax, Va.

[21] Appl. No.: 663,758

[22] Filed: Mar. 1, 1991

Related U.S. Application Data

[63] Continuation of Ser. No. 571,387, Aug. 23, 1990, abandoned.

[51] Int. Cl.$^5$ ................................................. C07C 5/13
[52] U.S. Cl. ...................................... 585/739; 585/751
[58] Field of Search ................................ 585/739, 751

[56] References Cited

U.S. PATENT DOCUMENTS

| | | | |
|---|---|---|---|
| 4,439,409 | 3/1984 | Puppe et al. | 562/60 |
| 4,734,539 | 3/1988 | Lawlor et al. | 585/739 |
| 4,855,530 | 8/1989 | LaPierre et al. | 585/739 |
| 4,962,250 | 10/1990 | Dessau et al. | 575/417 |

OTHER PUBLICATIONS

C. W. Cartwright and R. J. Stock, Oil & Gas Journal, 9/18/78, pp. 141–145.
G. L. Frischkorn, P. J. Kuchar and R. K. Olson, Energy Progress, vol. 8, No. 3, Sep. 1988, pp. 154–159.
Hydrocarbon Processing, Sep. 1988, p. 82.

*Primary Examiner*—Anthony McFarlane
*Assistant Examiner*—Nhat Phan
*Attorney, Agent, or Firm*—Alexander J. McKillop; Charles J. Speciale; Marina V. Schmeller

[57] ABSTRACT

The process relates to converting normal paraffins and/or mono-methyl branched paraffins, which are generally of low octane value, to more highly branched isoparaffins which are generally superior to normal paraffins in octane.

26 Claims, 1 Drawing Sheet

FIG. 1 ns to higher branched paraffins which are generally better octane boosters. By way of illustration, the significance of these reactions can be gleaned from a review of the following table of Octane Numbers of Pure Hydrocarons from "Catalysis," Vol. VI, P. H. Emmett (ed.) Copyright 1958 by Litton Educational Publishing Company:

ZEOLITE MCM-22 BASED CATALYST FOR PARAFFIN ISOMERIZATION

This is a continuation of copending application Ser. No. 571,387, filed on Aug. 23, 1990, now abandoned.

FIELD OF THE INVENTION

This invention relates to catalytic isomerization, and more particularly to a process for upgrading feedstocks containing normal and/or mono-methyl branched paraffins. Paraffin isomerization catalysts promote skeletal rearrangement of low octane linear paraffins and only slightly branched paraffins to higher octane, more highly branched paraffins.

BACKGROUND OF THE INVENTION

A unit process which is frequently encountered in petroleum refining is paraffin isomerization. Paraffin isomerization of linear (straight chain) paraffins produces branched chain paraffins. In such a process, as conventionally operated, low molecular weight $C_4$–$C_6$ paraffins are converted to iso-paraffins in the presence of an acidic catalyst such as aluminum chloride. Recently, $C_6+$, preferably $C_{10}+$ n-paraffins, have been isomerized, in the presence of large pore size zeolites to produce branched chain paraffins by skeletal rearrangement. The latter process can find application in dewaxing.

Isomerization is one of several reactions which occur in reforming of naphthas. Reforming of naphthas is undertaken to upgrade a low octane naphtha to a higher octane effluent. One of the octane enhancing reactions which occurs during reforming is the isomerization of n-paraffins to isoparaffins. Under the process conditions of reforming, other reactions which occur are aromatization (or dehydrocyclization), dehydrogenation, with some cracking.

Paraffin isomerization catalysts may also be employed as ring opening catalysts for removal of cyclic aromatic precursors from reformer feedstocks. For example, cyclohexane, a precursor to benzene, is rearranged over commercial paraffin isomerization catalysts to a mixture of branched paraffins. Branched paraffins are only partly aromatized in reforming whereas cyclohexane is completely converted to aromatics, mostly benzene. Application of paraffin isomerization catalysts for ring opening aromatics precursors will no doubt become more important as environmental regulations limiting aromatics in gasoline become more stringent.

SUMMARY OF THE INVENTION

The catalytic isomerization process of the invention is operated to increase the octane of low octane naphthas containing $C_6$–$C_{10}$ n-paraffins and/or mono-methyl branched paraffins, which under conventional reforming conditions, are the most difficult components to upgrade. A potential advantage of the process of the invention is an increase in liquid yields by minimizing, if not eliminating the cracking of $C_5+$ hydrocarbons which include $C_6$ to $C_{10}$ n-paraffins. Still another application of the isomerization process of the invention is to upgrade refinery streams rich in $C_4$–$C_6$ n-paraffins.

In accordance with the invention, the isomerization is undertaken in the presence of a catalyst comprising a dehydrogenation/hydrogenation metal and the zeolite MCM-22. During the isomerization these n-paraffinic and mono-methyl branched paraffinic components are isomerized to higher branched paraffins which are generally better octane boosters. By way of illustration, the significance of these reactions can be gleaned from a review of the following table of Octane Numbers of Pure Hydrocarons from "Catalysis," Vol. VI, P. H. Emmett (ed.) Copyright 1958 by Litton Educational Publishing Company:

| Octane Numbers of Pure Hydrocarbons | |
|---|---|
| Hydrocarbon Paraffins: | Blending Research Octane Number (clear) |
| n-heptane | 0 |
| 2-methylhexane | 41 |
| 3-methylhexane | 56 |
| 2,2-dimethylpentane | 89 |
| 2,3-dimethylpentane | 87 |
| 2,2,3-trimethylbutane | 113 |

DETAILED DESCRIPTION OF THE INVENTION

Feedstock

The feedstock for the process is one which contains significant amounts of $C_5+$ normal and/or slightly branched paraffins, especially normal and/or slightly branched paraffins in the $C_{65}$–$C_{10}$ range. Accordingly, normal hexane and normal heptane as well as the various mono-methyl branched isomers alone or in admixture may be employed as the feedstock in the process of the invention. In addition, the feedstock may contain monocyclic aromatic compounds and/or cyclic paraffins, such as cyclohexane.

The feedstock to the isomerization process can be straight-run, thermal, or catalytically cracked naphtha. Typically, naphthas boil at 800° to 400°F. Preferably, for high increases in octane numbers of the feed, the charge to the process is a naphtha rich in $C_6$ to $C_{10}$ paraffins. Naphtha rich in $C_6$ and $C_7$ paraffins is generally difficult to reform selectively using conventional catalysts (such as chlorided Pt-alumina). Naphthas can be obtained by separating the charge into two fractions: a light naphtha and a heavy naphtha. Conventionally such separation is by distillation. The boiling range of the light naphtha is from about 80° F. to about 400° F. and the boiling range of the heavy naphtha will be from up to about 650° F. The light naphtha will be rich in $C_6$–$C_{10}$ paraffins, and specifically $C_6$ and $C_7$ paraffins. In accordance with one embodiment when the light naphtha is upgraded in accordance with the invention, the heavy naphtha will be processed by conventional reforming.

Generally, the feeds of the process of the invention do not contain bicyclic and polycyclic aromatics; bicyclic and polycyclic aromatics are commonly found in the higher boiling fractions (IBP over 340° C.), than those which are used as feeds in the process of the invention. Single ring (monocyclic) aromatics which are readily hydrogenated over the metal component of the catalyst can be tolerated and at the higher end of the range of temperature conditions of the process of the invention may be subject to ring opening to form branched chain paraffin compounds. The aromatic content may, for preference, be held below 10 weight percent although slightly greater amounts up to about 20 weight percent might be tolerated if the proportion of monocyclic aromatics is sufficiently high and if a sufficiently strong hydrogenation component such as platinum is present on the catalyst.

In the specific embodiment of isomerizing lower molecular weight hydrocarbons, the feedstock is a refinery stream which contains significant amounts of $C_4$-$C_6$ n-paraffins.

Catalyst

The catalyst composition employed in the catalytic isomerization of normal and/or slightly branched paraffins, in accordance with the invention comprises a dehydrogenation/hydrogenation metal and MCM-22 zeolite.

The zeolite is to be used in intimate combination with a dehydrogenation/hydrogenation component such as tungsten, vanadium, molybdenum, rhenium, nickel, cobalt, chromium, manganese, or a noble metal such as platinum or palladium. Such component can be introduced in the catalyst composition by way of cocrystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex. The amount of the dehydrogenation/hydrogenation component in the catalyst composition can range from 0.01 to 20 weight percent of the composition.

The zeolite MCM-22 is readily identified by its characteristic X-ray diffraction pattern. In its calcined form, this synthetic porous crystalline material component employed in the catalyst composition useful in the process of this invention is characterized by an X-ray diffraction pattern including the following lines:

TABLE A

| Interolanar d-Spacing (A) | Relative Intensity, $I/I_o \times 100$ |
| --- | --- |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
| --- | --- |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0-20
M=20-40
S=40-60
VS=60-100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for isomerization. These may include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the process of this invention, the zeolite crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, n terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free H20 and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the crystalline material with another material which is resistant to the temperatures and other conditions employed in the process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the catalyst of the invention may be increased by steaming. U.S. Pat. Nos. 4,663,492; 4,594,146; 4,522,929; and 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5–100% steam at a temperature of at least about 300° C. (e.g., 300°–650° C.) for at least one hour (e.g., 1–200 hours) at a pressure of 101–2,500 kPa. In a more particular embodiment, the catalyst can be made to undergo steaming with 75–100% steam at 315°–500° C. and atmospheric pressure for 2–25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

The process of this invention can be carried out as a batch-type, semi-continuous or continuous operation utilizing a fixed, fluidized or moving bed catalyst system.

In order to more fully illustrate the isomerization process of this invention and the manner of practicing same, the following examples are presented. In the examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM- 22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant $=0.016$ $\sec^{-1}$) The Alpha Test is described in U.S. Pat. No. 3,354,078, in the Journal of Catalysis. Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis. Vol. 61, p. 395.

Process Conditions

The feedstock is contacted with the catalyst composition of the invention in the presence or absence of added hydrogen at elevated temperature and pressure. Temperatures are normally from about 250° to 700° F., preferably from about 400° F. to 600° F. Because cracking reactions tend to increase with increasing temperatures, lower temperatures will normally be preferred in order to favor the isomerization over the cracking reactions. Pressures range from atmospheric up to 1000 psig. The preferred range is from 50 to 500 psig. Weight hourly space velocity is generally from 0.1 to 50 $hr^{-1}$, more usually 0.2 to $10 hr^{-1}$. If additional hydrogen is cofed with the feedstock, the hydrogen:feedstock molar ratio is generally from 1:1 to 10:1.

The process is preferably carried out in the presence of hydrogen, both to inhibit catalyst aging and to promote the isomerization reactions which are thought to proceed through an unsaturated intermediate.

The conversion may be conducted by contacting the feedstock with a fixed stationary bed of catalyst, a fixed fluidized bed or with a transport bed. A simple configuration is a trickle-bed operation in which the feed is allowed to trickle through a stationary fixed bed. With such a configuration, it is desirable to initiate the reaction with fresh catalyst at a moderate temperature which is raised if the catalyst ages, in order to maintain catalytic activity. The catalyst may be regenerated by contact at elevated temperature with hydrogen gas, for example, or by burning in air or other oxygen-containing gas.

EXAMPLES

The following Examples 1-14 show synthesis and characterization of a catalytic material useful in the present invention, which is commonly referred to as MCM-22.

Examples A-C are particularly directed to illustrating the invention.

EXAMPLE A

The MCM-22 catalyst used in this study was prepared according to the following procedure. One part sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution wa added to 8.55 parts of Ultrasil, a precipitated, spray-dried silica (90% $SiO_2$).

The reaction mixture had the following composition, in mole ratios:
$SiO_2/Al_2O_3 = 30.0$
$OH/SiO_2 = 0.18$
$H_2O/SiO_2 = 44.9$
$Na/SiO_2 = 0.18$
$R/SiO_2 = 0.35$
where R is hexamethyleneimine.

The mixture was crystallized in a stainless steel reactor, with stirring, at 150° C. for 7 days. The crystalline product was filtered, washed with water, dried at 120° C. and calcined for 20 hours at 538° C. The sorption capacities of the calcined material were measured to be:
$H_2O$ 15.2 wt%
Cyclohexane 14.6 wt%
n-Hexane 16.7 wt%

The surface area of the zeolite was measured to be 494 $m^2/g$.

EXAMPLE B

A sample of platinum exchanged MCM-22 was prepared by the following procedure. The MCM-22 prepared in accordance with the above procedure was exchanged with ammonium nitrate. To this was added an aluminum oxide binder. The mixture was mulled, extruded and dried at 250° F. It was then calcined in nitrogen at 1000° F. for 3 hours. After humidification the mixture was exchanged with 1N ammonium nitrate, dried and calcined again in nitrogen at 1000° F. The mixture was again humidified, exchanged with $Pt(NH_3)_4Cl_2$ solution for 8 hours, rinsed, dried and calcined at 660° F. in air. Catalyst properties are given in Table 1.

TABLE 1

| PT/MCM-22 CATALYST PROPERTIES | |
|---|---|
| Composition, wt % | |
| Zeolite MCM-22 | 65 |
| Platinum | 0.66 |
| Density, g/cc | |
| Packed | 0.45 |
| Particle | 0.73 |
| Real | 2.60 |
| Physical Properties | |
| Pore Volume, cc/g | 0.99 |
| Surface Area, $m^2/g$ | 372 |
| Avg. Pore Diameter, A | 106 |

EXAMPLE C

The activity of the Pt/MCM-22 catalyst was compared against a Pt/silica-alumina catalyst (0.6 wt% Pt) and UOP's I-7, a commercially available noble metal containing mordenite-based isomerization catalyst, using a microunit equipped with a ⅜" downflow stainless steel reactor. In a typical experiment, 10 cc of sized catalyst (14/24 mesh) were loaded into the reactor and reduced in hydrogen at 800° F. for 2 hours. The reactor was cooled to 450° F. and pressurized to 100 psig with hydrogen. A n-hexane feed was then introduced at 1 gram/gram cat/hr with a 2/1 mol/mol hydrogen cofeed. The product from the reactor was analyzed with an on-line gas chromatograph equipped with a 30 meter megabore DB-1 column.

Figure 1:
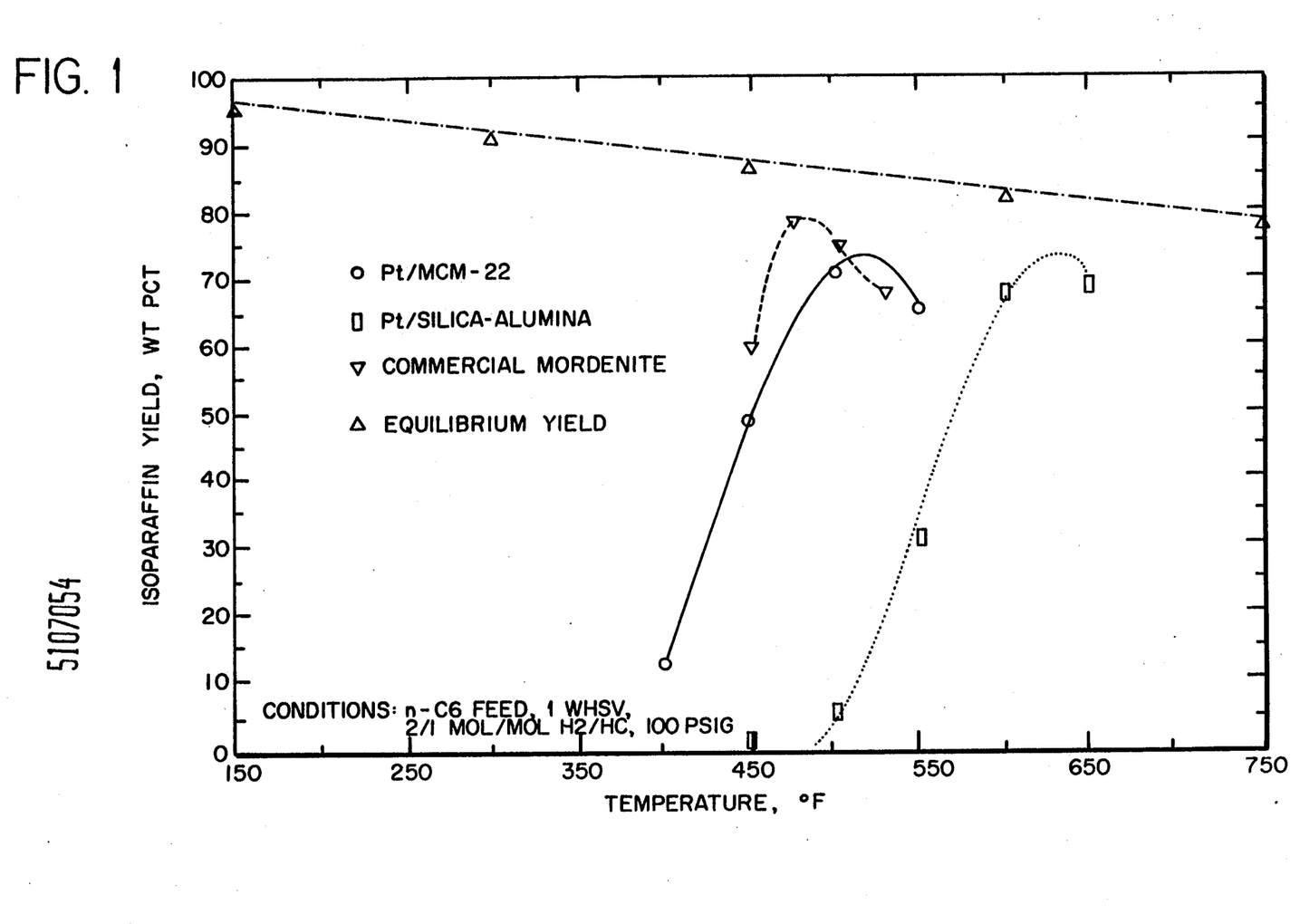
FIG. 1 is a graph of the plot of isoparaffin production vs. temperature.

The yields of isoparaffin products with Pt/MCM-22, Pt/silica-alumina and UOP's I-7, a commercially available noble metal containing mordenite-based isomerization catalyst, are plotted as a function of temperature in FIG. 1. The Pt/MCM-22 and I-7 catalysts showed comparable activity and afforded near equilibrium conversion of n-hexane at 475°–500° F. while the Pt/silica-alumina catalyst required a much higher temperature, 625° F., for near equilibrium conversions of n-hexane.

Paraffin isomerization is an important commercial process for upgrading low octane, light straight run naphthas. The Pt/MCM-22 catalyst noted herein was found to be significantly more active than an amorphous Pt/silica-alumina catalyst for paraffin isomerization. Furthermore, the activity of Pt/MCM-22 for paraffin isomerization was comparable to that of UOP's I-7, a commercially available noble metal containing mordenite-based isomerization catalyst.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

$SiO_2Al_2O_3 = 30.0$
$OH^-/SiO_2 = 0.18$
$H_2O/SiO_2 = 44.9$
$Na/SiO_2 = 0.18$
$R/SiO_2 = 0.35$ where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

$H_2O$ = 15.2 wt. %
Cyclohexane = 14.6 wt. %
n-Hexane = 16.7 wt. %

The surface area of the calcined crystalline material was measured to be 494 $m^2/g$.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |

$SiO_2Al_2O_3$, mole ratio = 21.1

TABLE E

| Degrees 2-Theta | d-Spacing (A) | Interplanar $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |

TABLE E-continued

| Degrees 2-Theta | d-Spacing (A) | Interplanar $I/I_o$ |
|---|---|---|
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3–5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| | Example | | |
|---|---|---|---|
| | 3 | 4 | 5 |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.60 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution were added 8.54 parts of Ultrasil silica. The mixture was crystallized with agitation at 145° C. for 59 hours and the resultant product was water washed and dried at 120° C.

Product chemical composition (uncalcined), surface area and adsorption analyses results were as set forth in Table G:

TABLE G

| Product Composition | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| | Exchange Ions | | |
|---|---|---|---|
| Ionic Composition, wt. % | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite has very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

$SiO_2/B_2O_3 = 6.1$
$OH^-/SiO_2 = 0.06$
$H_2O/SiO_2 = 19.0$
$K/SiO_2 = 0.06$
$R/SiO_2 = 0.30$ where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

$H_2O$ (12 Torr) = 11.7 wt. %
Cyclohexane (40 Torr) = 7.5 wt. %
n-Hexane (40 Torr) = 11.4 wt. %

The surface area of the calcined crystalline material was measured (BET) to be 405$m^2/g$.

The chemical composition of the uncalcined material was determined to be as follows:

N = 1.94 wt. %
Na = 175 ppm
K = 0.60 wt. %
Boron = 1.04 wt. %
$Al_2O_3$ = 920 ppm
$SiO_2$ = 75.9 wt. %
Ash = 74.11 wt. %
$SiO_2Al_2O_3$, molar ratio = 1406
$SiO_2/(Al+B)_2O_3$, molar ratio = 25.8

EXAMPLE 12

A portion of the calcined crystalline product of Example was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

$SiO_2B_2O_3 = 12.3$
$OH^-/SiO_2 = 0.056$
$H_2O/SiO_2 = 18.6$
$K/SiO_2 = 0.056$
$R/SiO_2 = 0.30$ where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

H$_2$O (12 Torr) = 14.4 wt. %
Cyclohexane (40 Torr) = 4.6 wt. %
n-Hexane (40 Torr) = 14.0 wt. %

The surface area of the calcined crystalline material was measured to be 438m$^2$/g.

The chemical composition of the uncalcined material was determined to be as follows:

| Component | Wt. % |
|---|---|
| N | 2.48 |
| Na | 0.06 |
| Boron | 0.83 |
| Al$_2$O$_3$ | 0.50 |
| SiO$_2$ | 73.4 |

SiO$_2$/Al$_2$O$_3$, molar ratio = 249
SiO$_2$/(Al + B)$_2$O$_3$, molar ratio = 28.2

EXAMPLE 14

A portion of the calcined crystalline product of Example 13 was tested in the Alpha Test and found to have an Alpha Value of 5.

EXAMPLE 15

Zeolite MCM-22 was prepared by adding 4.49 parts quantity of hexamethyleneimine to a mixture containing 1.00 part sodium aluminate, 1.00 part 50% NaOH, 8.54 parts Ultrasil VN3 and 44.19 parts deionized H$_2$O. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized H$_2$O and dried.

A portion of the zeolite crystals was combined with Al$_2$O$_3$ to form a mixture of 65 parts, by weight, zeolite and 35 parts Al$_2$O$_3$. Water was added to this mixture to allow the resulting catalyst to be formed into extrudates. The catalyst was activated by calcining in nitrogen at 540° C. (1000° F.), followed by aqueous ammonium nitrate exchange and calcining in air at 540° C. (1000° F.).

What is claimed is:

1. A process for isomerizing a paraffin having 4 to carbon atoms by skeletal rearrangement to an isoparaffin having the same number of carbon atoms, comprising
    contacting the paraffin with a catalyst composition comprising a dehydrogenation/hydrogenation metal and a porous crystalline material, which exhibits the X-ray diffraction pattern of Table A of the specification,
    wherein the dehydrogenation/hydrogenation metal is present in an amount ranging from 0.01 to 10 weight percent of said catalyst composition,
under contacting conditions comprising a temperature ranging from about 250° to 700° F., a pressure ranging from atmospheric up to 1000 psig; a weight hourly space velocity ranging from 0.1 to 50 hr$^{-1}$, and a hydrogen:feedstock molar ratio from 0:1 to 10:1; and
    recovering said isoparaffin.

2. The process of claim 1, wherein the temperature is from about 400° F. to 600° F.

3. The process of claim 1, wherein the pressure ranges from atmospheric to 500 psig.

4. The process of claim 1, wherein the weight hourly space velocity is from 0.2 to 10 hr$^{-1}$.

5. The process of claim 1, wherein the hydrogen:feedstock molar ratio is from 0.5:1 to 10:1.

6. The process of claim 1, wherein the paraffin is admixed with cyclic paraffin(s) or monocyclic aromatic compound(s).

7. The process of claim 6, which includes recovering isoparaffin(s) containing an amount of cyclic compounds which is less than the cyclic compounds admixed with said paraffins.

8. A process for upgrading a naphtha feedstock having a boiling range of from 80° to 400° F. and containing at least one paraffin having 4 to 10 carbon atoms and wherein the paraffin is an n-paraffin and/or a mono-methyl branched paraffin, comprising
    contacting the naphtha containing n-paraffin and/or mono-methyl branched paraffin containing naphtha with a catalyst composition comprising a dehydrogenation/hydrogenation metal and a porous crystalline material, which exhibits the X-ray diffraction pattern of Table A of the specification,
    wherein the dehydrogenation/hydrogenation metal is present in an amount ranging from 0.01 to 10 weight percent of said catalyst composition,
under contacting conditions comprising a temperature ranging from about 250° to 700°F., a pressure ranging from atmospheric up to 1000 psig; a weight hourly space velocity ranging from 0.1 to 50 hr$^{-1}$, and a hydrogen:feedstock molar ratio from 0:1 to 10:1; and
    recovering an effluent in which the amount of said n-paraffin is less than that in the feedstock.

9. The process of claim 8, wherein the temperature is from about 400° F. to 600° F.

10. The process of claim 8, wherein the pressure ranges from atmospheric to 500 psig.

11. The process of claim 8, wherein the weight hourly space velocity is from 0.2 to 10 hr$^{-1}$.

12. The process of claim 8, wherein the hydrogen:feedstock molar ratio is from 0.5:1 to 10:1.

13. The process of claim 8, wherein the naphtha contains cyclic paraffin(s) and/or monocyclic aromatic compound(s).

14. The process of claim 13, which includes recovering an effluent containing an amount of cyclic compounds which is less than the cyclic compounds in said naphtha feedstock.

15. A process for upgrading a naphtha feedstock having a boiling range of from 80° to 400° F. and containing at least one paraffin having 4 to 10 carbon atoms, and having an octane value of from 30 to 80 comprising
    contacting the naphtha containing paraffin with a catalyst composition comprising a dehydrogenation/hydrogenation metal and a porous crystalline material, which exhibits the X-ray diffraction pattern of Table A of the specification,
    wherein the dehydrogenation/hydrogenation metal is present in an amount ranging from 0.01 to 10 weight percent of said catalyst composition,
under contacting conditions comprising a temperatures ranging from about 250° to 700°F., a pressure ranging from atmospheric up to 1000 psig; a weight hourly space velocity ranging from 0.1 to 50 hr$^{-1}$, and a hydrogen:feedstock molar ratio from 0:1 to 10:1; and recovering an effluent which has an octane value greater than that of the feedstock.

16. The process of claim 15, wherein the naphtha feedstock contains cyclic paraffin(s) and/or monocyclic aromatic compound(s).

17. The process of claim 16, which includes recovering an effluent containing an amount of cyclic compounds which is less than the cyclic compounds in said naphtha feedstock.

18. The process of claim 1, wherein the porous crystalline material exhibits the X-ray diffraction pattern of Table D of the specification.

19. The process of claim 8, wherein the porous crystalline material exhibits the X-ray diffraction pattern of Table D of the specification.

20. The process of claim 15, wherein the porous crystalline material exhibits the X-ray diffraction pattern of Table D of the specification.

21. The process of claim 1, wherein the porous crystalline material exhibits the X-ray diffraction pattern of Table B of the specification.

22. The process of claim 8, wherein the porous crystalline material exhibits the X-ray diffraction pattern of Table B of the specification.

23. The process of claim 15, wherein the porous crystalline material exhibits the X-ray diffraction pattern of Table B of the specification.

24. The process of claim 1, wherein the porous crystalline material exhibits the X-ray diffraction pattern of Table C of the specification.

25. The process of claim 8, wherein the porous crystalline material exhibits the X-ray diffraction pattern of Table C of the specification.

26. The process of claim 15, wherein the porous crystalline material exhibits the X-ray diffraction pattern of Table C of the specification.

* * * * *

UNITED STATES PATENT AND TRADEMARK OFFICE
CERTIFICATE OF CORRECTION

PATENT NO. : 5,107,054

DATED : April 21, 1992

INVENTOR(S) : Kenneth J. Del Rossi et al.

It is certified that error appears in the above-identified patent and that said Letters Patent is hereby corrected as shown below:

Column 15, line 49 (claim 1), before "carbon" insert --10--.

Column 16, line 20, (claim 8), delete "containing naphtha".

Signed and Sealed this

Third Day of August, 1993

*Attest:*

MICHAEL K. KIRK

*Attesting Officer*      *Acting Commissioner of Patents and Trademarks*